United States Patent [19]
Chakeres

[11] Patent Number: 6,159,221
[45] Date of Patent: Dec. 12, 2000

[54] STEREOTACTIC APPARATUS AND METHODS

[75] Inventor: Donald W. Chakeres, Columbus, Ohio

[73] Assignee: The Ohio State University, Columbus, Ohio

[21] Appl. No.: 09/200,269
[22] Filed: Nov. 25, 1998
[51] Int. Cl.[7] ................................................. A61B 5/055
[52] U.S. Cl. ............................................ 606/130; 600/429
[58] Field of Search ............................. 606/130; 600/429

[56] References Cited

U.S. PATENT DOCUMENTS

| | | | |
|---|---|---|---|
| 5,437,280 | 8/1995 | Hussman | 606/130 |
| 5,447,154 | 9/1995 | Cinguin et al. | 600/429 |
| 5,628,315 | 5/1997 | Vilsmeier et al. | 606/130 |
| 5,678,549 | 10/1997 | Heywang Koebrunner et al. | 606/130 |
| 5,690,108 | 11/1997 | Chakeres | 600/429 |

Primary Examiner—Paul J. Hirsch
Attorney, Agent, or Firm—Standley & Gilchrist LLP

[57] ABSTRACT

Apparatus is disclosed for assisting in the location, vectoring, and insertion of a needle-like medical device relative to a patient's body using medical imaging equipment that produces patient cross-sectional images and that has a monitor which displays produced cross-section images. Included image-conspicuous, double-V reference patterns are sectioned and displayed at the equipment monitor in a manner readily identifying and quantifying position changes necessary to assure accurate needle-device location, vectoring, and insertion.

11 Claims, 10 Drawing Sheets

STEREOTACTIC APPARATUS AND METHODS

CROSS-REFERENCES

None.

FIELD OF THE INVENTION

This invention relates generally to interventional medicine, and particularly concerns stereotactic apparatus and stereotactic methods which may be advantageously utilized by a physician in conjunction with cross-sectioning types of medical imaging equipment such as computed tomography imaging (CTI) equipment and magnetic resonance imaging (MRI) equipment. The invention additionally conveniently, accurately, and inexpensively aids the physician in timely and manually accomplishing the steps of properly locating, vectoring, and inserting a needle-like medical device at, toward, and into a targeted patient anatomic feature while the patient is being imaged.

BACKGROUND OF THE INVENTION

Medical science researchers and practitioners are increasingly giving more attention to the development of less-intrusive diagnostic and therapeutic medical procedures for use in the care of patients, thereby avoiding otherwise required conventional surgery and the consequent high costs of patient hospitalization. Examples of such less-intrusive diagnostic and therapeutic procedures include laparoscopic surgery, placement of drainage catheters, fine needle aspiration biopsies, stereotactic radiation therapy, needle injection of drugs (including radiological drugs), soft tissue destruction by laser beam, trocar insertion of cannulae, and the like, each accomplished in relation to a particular patient's anatomic target and preferred vector path.

Medical equipment manufacturers also have given attention to the development and marketing of apparatus for use in effecting less-intrusive diagnostic and therapeutic medical procedures, and often such apparatus has been comparatively complex in design, costly to obtain, and difficult and time-consuming to utilize.

One of the more recent stereotactic apparatus developments is disclosed and claimed in my U.S. Pat. No. 5,690,108, granted Nov. 25, 1997.

Experience since the filing date of the patent application resulting in U.S. Pat. No. 5,690,108, however, has led to the conclusion that in some applications or instances, e.g. such as taking biopsy specimens, etc. from a human female breast, the earlier stereotactic apparatus may be significantly improved, and such is one of the objectives of the present invention.

Other advantages and objects of the invention will become apparent during a careful and thoughtful consideration of the descriptive materials which follow.

SUMMARY OF THE INVENTION

The present invention basically involves, in addition to use of a co-operating, cross-sectional type (CT or MR) medical imaging system, use of physician assist stereotactic apparatus essentially comprised of a base subassembly having an image-conspicuous reference pattern, a body-part compression plate subassembly movably supported by the base subassembly and having an internal opening through which a needle-like medical device may be passed, and a remotely controlled, needle-device locator subassembly fixedly carried by the compression plate subassembly and carrying a removably-installed needle-device guide. The apparatus base subassembly is normally supported by the imaging equipment patient support table near that region of the patient's body that is to be sectionally imaged, and need only be initially approximately correctly oriented relative to the imaging equipment sectioning plane and the anatomic target of interest within the patient.

The apparatus base subassembly includes a frame element, and within the frame element, a base element carrying a double-V, image-conspicuous, planar reference pattern. Such planar reference pattern is cross-sectioned and imaged by the medical imaging equipment during patient cross-sectional imaging. The base element with reference pattern is rotatable relative to the base frame element, relative to the patient's body, and relative to the imaging equipment about a substantially vertical axis that is parallel to the imaging equipment's vertical axis.

The base member double-V planar reference pattern has an image-conspicuous configuration and is the source of images that encode apparatus placement and angularity information relative to the imaging equipment X-Y sectioning plane, such placement and angularity information being obtained by inferential interpretation of the displayed reference pattern images solely using direct image measurements, simple logic, and simple arithmetic for an interactive procedure. Calibrated scales are provided integral with the base subassembly to assist in correcting reference pattern angularity relative to the imaging equipment sectioning plane. Apparatus base member positional and/or angularity values derived from the displayed reference pattern images preferably are scaled on a one hundred percent (100%) basis to apparatus calibrated scale values thereby facilitating effective apparatus position adjustments.

The apparatus body-part compression plate subassembly has a relatively large interior opening through which a variably positioned needle-device may be passed, and fixedly supports a needle-device locator subassembly which partially surrounds the interior opening. Also, the compression plate subassembly is movably mounted upon the apparatus base element in a manner that will assure constant parallelism between the compression plate, the apparatus base subassembly, and the imaging machine patient support table and horizontal reference plane.

The needle-device locator subassembly includes a readily removable and disposable needle-device guide element that is moved in horizontal co-ordinate directions by a remote control powered either manually or by automated servo control actuators. Importantly, the readily removable needle-device guide element is provided with a double-V, image-conspicuous, reference patterns whose screen images significantly aid the physician-user in truly vertically vectoring the needle-device and in visually quantitatively determining the depth of needle-device penetration that is required to reach the targeted patient-image anatomical area.

Through a preferred method of manipulation of the invention apparatus a physician is able to readily monitor in real-time, or in near real-time depending upon the type of imaging equipment being used, the accuracy of needle-device location, vectoring, and insertion merely by a careful inspection and interpretation of the imaging equipment cross-sectioning plane reference pattern section displays.

Other advantages associated with my invention will become apparent from the drawings and detailed description which follow.

DETAILED DESCRIPTION

Figure 1:
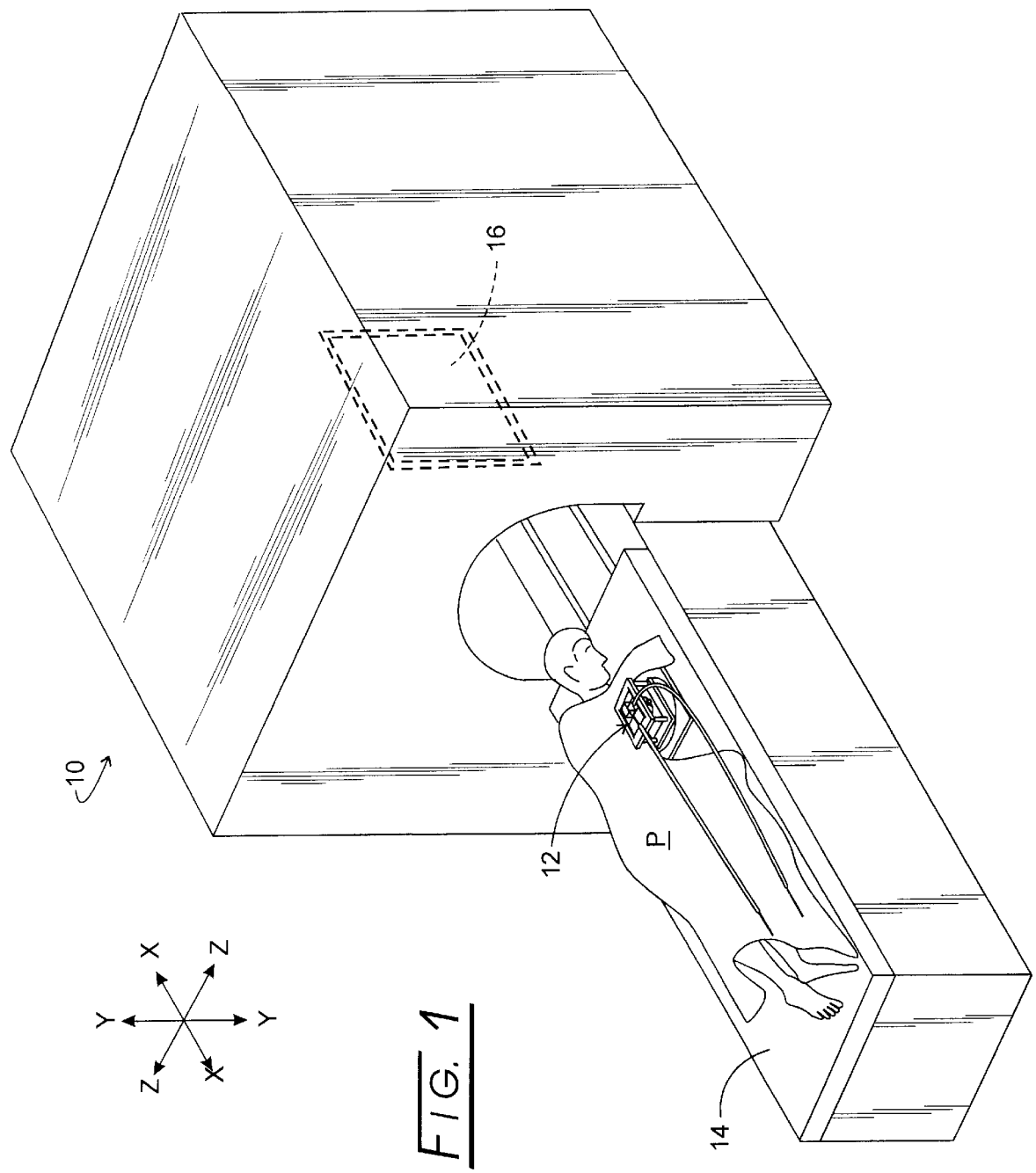
FIG. 1 is a schematic perspective view of MRI medical imaging equipment showing the initial positional relationship between a patient, the equipment patient support table, the equipment cross-sectional imaging plane, and the stereotactic apparatus of the present invention.

FIG. 1 of the drawings schematically illustrates a unit of magnetic resonance image (MRI) type cross-sectioning medical imaging equipment 10 with which the stereotactic apparatus 12 of the present invention may be utilized to assist the using physician in advantageously locating, vectoring, and inserting a medical needle-device relative to a patient anatomical target of interest. As previously suggested, equipment 10 might also take the form of a unit of computed tomography image (CTI) type of medical imaging equipment or other body cross-sectional imaging system. Such equipment typically is provided with a patient table 14 upon which the patient P to receive treatment is appropriately positioned. In most cross-sectional imaging equipment arrangements, the patient support table 14 generally may be incrementally indexed along its longitudinal axis to any of numerous different and repeatable positions at which the cross-sectional imaging plane 16 of the equipment intersects the patient's body (and stereotactic apparatus 12) at different points of anatomical interest.

In other forms of such medical imaging equipment, the patient support table remains in a transiently fixed position and the equipment scanner and cross-sectional imaging plane are moved relative to the table as a gantry. In the case of MRI imaging equipment, images of many different patient sectional planes can be obtained without moving either the patient or the equipment so long as the patient's body region of interest is located generally in the center of the equipment magnet/magnetic field. Also, FIG. 1 additionally schematically illustrates the conventional X-Y-Z coordinate axis scheme that pertains to equipment 10 and that is sometimes referred to describe particular angular and directional relationships. Note that the equipment cross-sectional imaging plane 16 corresponds to the X-Y coordinate plane and that the longitudinal axis of the patient support table 14 parallels the X coordinate axis.

The drawings do not illustrate the inclusion and positioning of a conventional equipment cathode ray tube monitor that appropriately displays the equipment-generated patient cross-sectional images including an image that contains the patient anatomical target of particular interest.

Throughout the specification and claims of this application the repeated use of specific co-ordinate directions is intended in a relative sense and not an absolute sense. Different equipment construction or operation modifications may be effected that result in changes of absolute co-ordinate direction without a relative change in co-ordinate direction.

Figure 2:
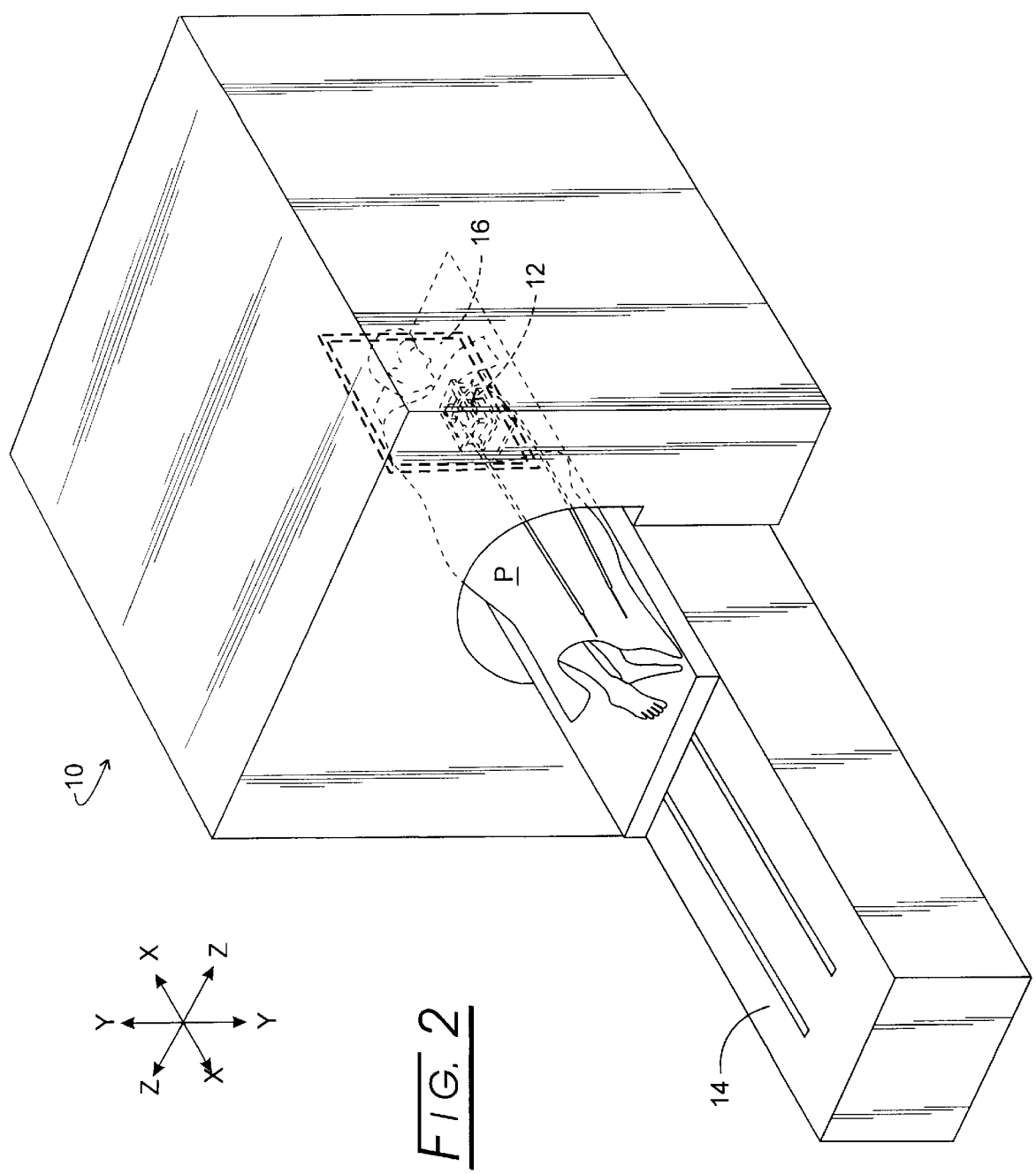
FIG. 2 is a view similar to FIG. 1 but illustrating the positional relationship after the patient and invention stereotactic apparatus have been moved with the patient support table to intersect the equipment cross-sectional imaging plane for imaging purposes.
Figure 3:
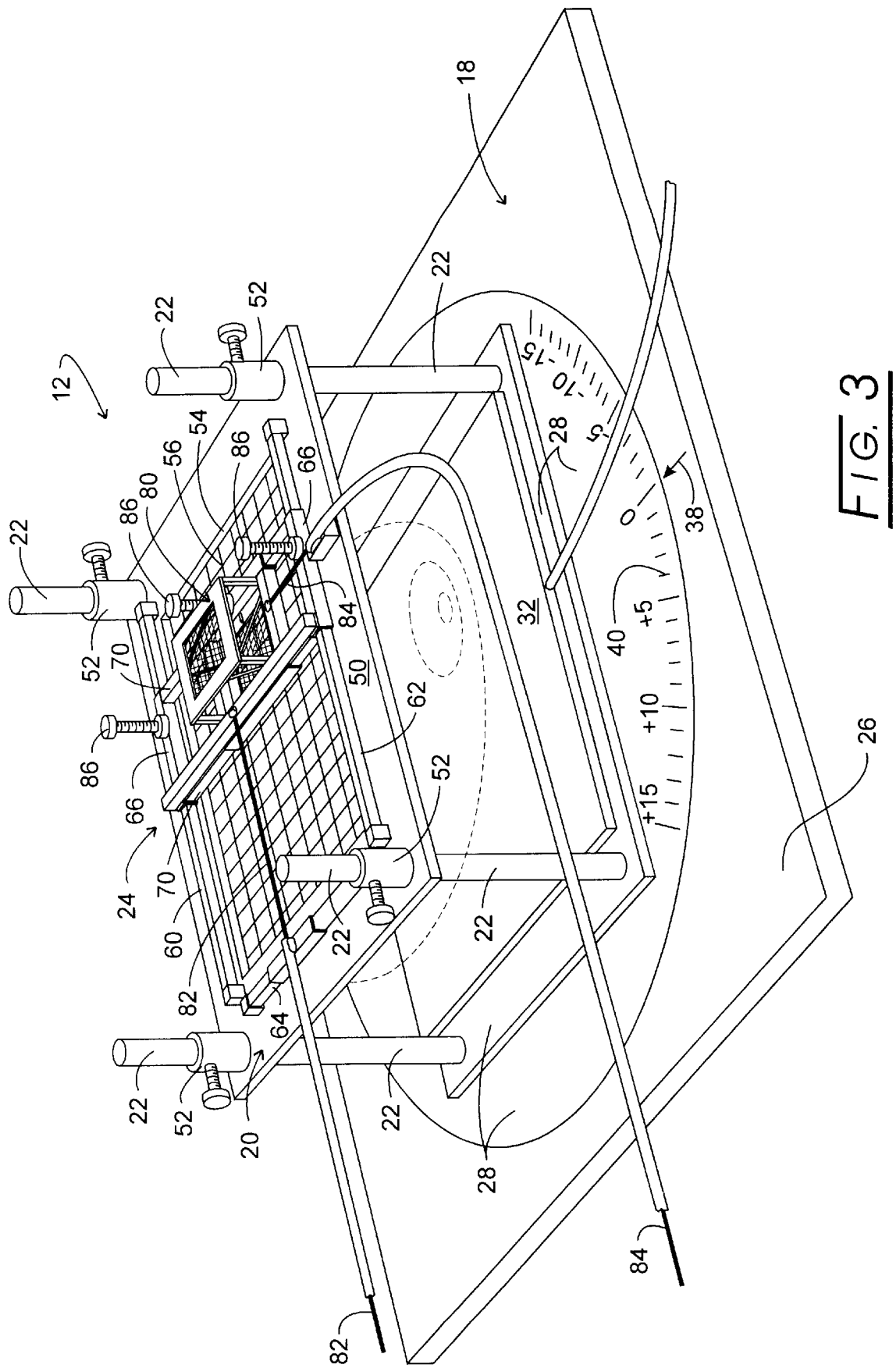
FIG. 3 is a more-detailed perspective view of the preferred embodiment of the stereotactic apparatus of FIGS. 1 and 2.
Figure 4:
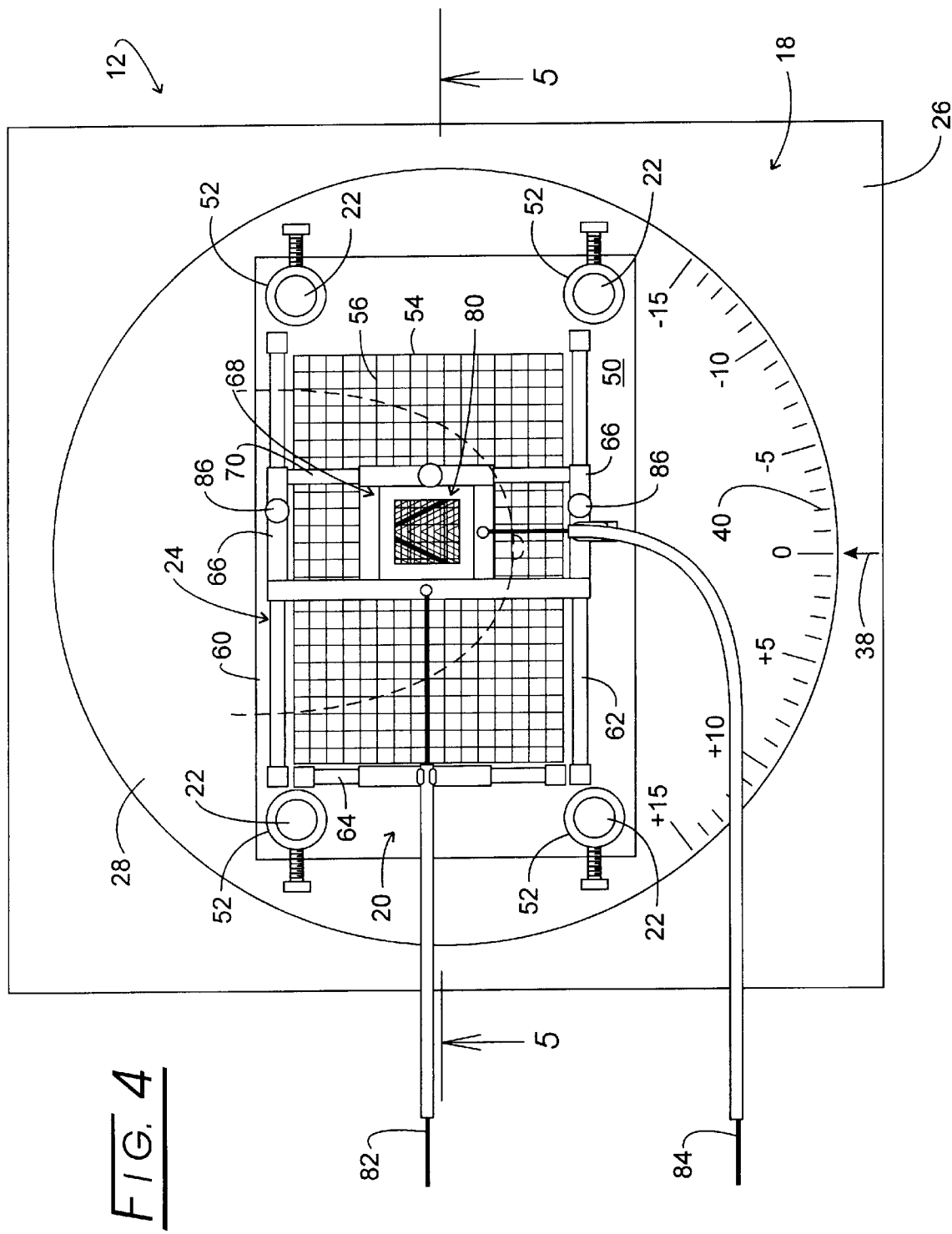
FIG. 4 is a plan view of the FIG. 3 stereotactic apparatus.

FIG. 2 illustrates the FIG. 1 component parts after the patient P and equipment support table 14 have moved to a position whereat equipment cross-sectional imaging plane images appearing on the equipment monitor screen intersect the patient's anatomical target of interest. In the drawings the patient P is shown as being in a decubitus position as for procedures involving the human female breast. However the stereotactic apparatus of the present invention may be utilized for medical procedures involving and other parts of the human body such as head, abdomen and extremities.

Referring to FIGS. 3 through 6, stereotactic apparatus 12 is more clearly illustrated as being basically comprised of base subassembly 18, movable compression plate subassembly 20 that cooperates with vertical support posts 22 mounted on subassembly 18, and needle-device locator subassembly 24 mounted on compression plate subassembly 20.

Base subassembly includes a frame member 26, a base member 28 positioned within and rotatable relative to frame member 26, and double-V reference pattern 30 (FIGS. 5 and 6) which is shown affixed to the underside of an equipment surface coil antenna 32 mounted on base member 28. Where pattern 30 is affixed to imaging equipment element 32 it must be with assurance that element 32 rotates with base member 28 when that member is rotated as for angularity adjustment purposes. Otherwise, double-V reference pattern may be directly affixed to base member 28. Frame member 26 can be retained in position on equipment patient support table 14 by removable tape or other functionally equivalent means. Such frame member retention minimizes the likelihood of assist apparatus 12 accidentally being moved relative to patient P during use.

Figure 5:
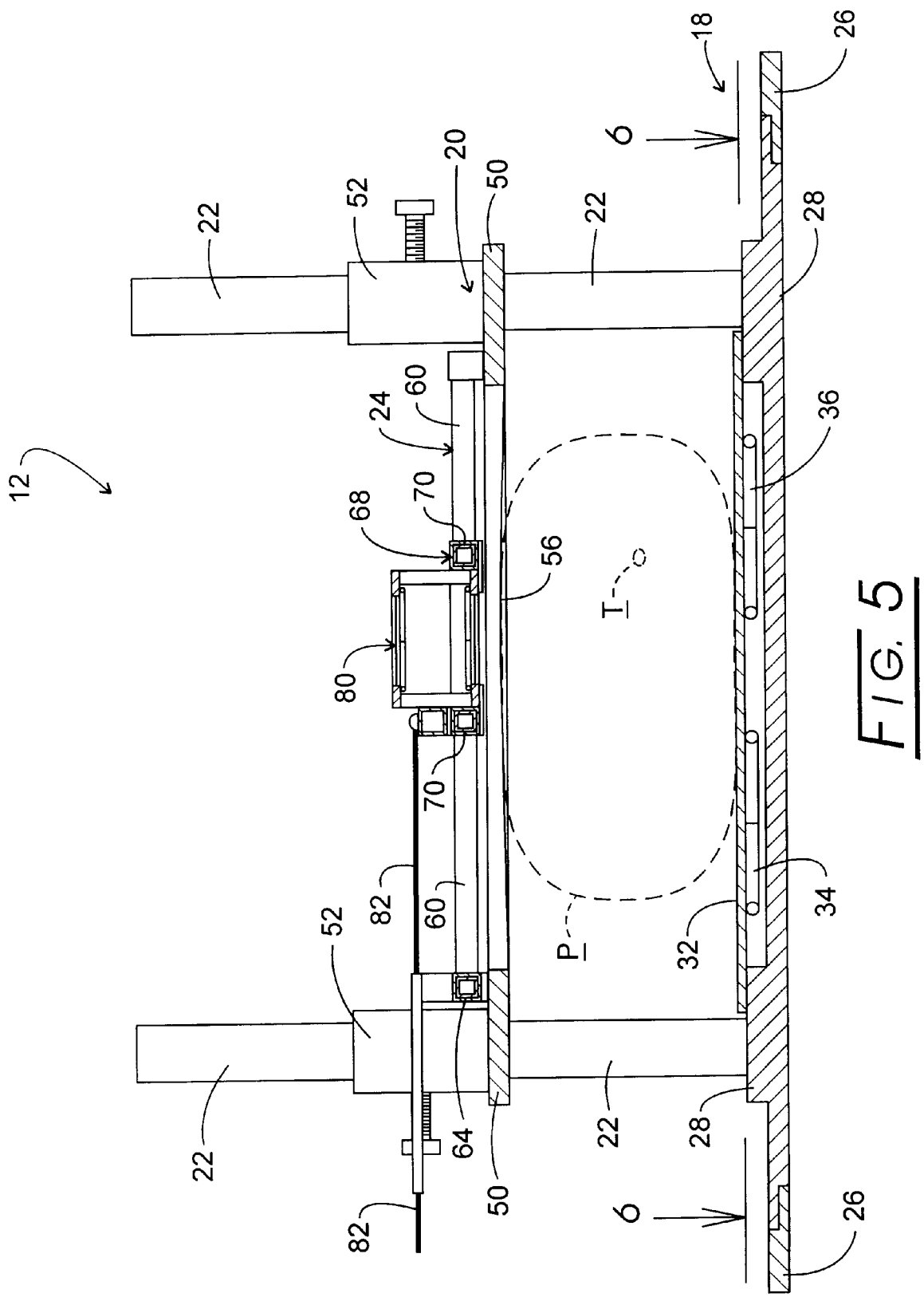
FIG. 5 is a section view taken at line 5—5 of FIG. 4.
Figure 6:
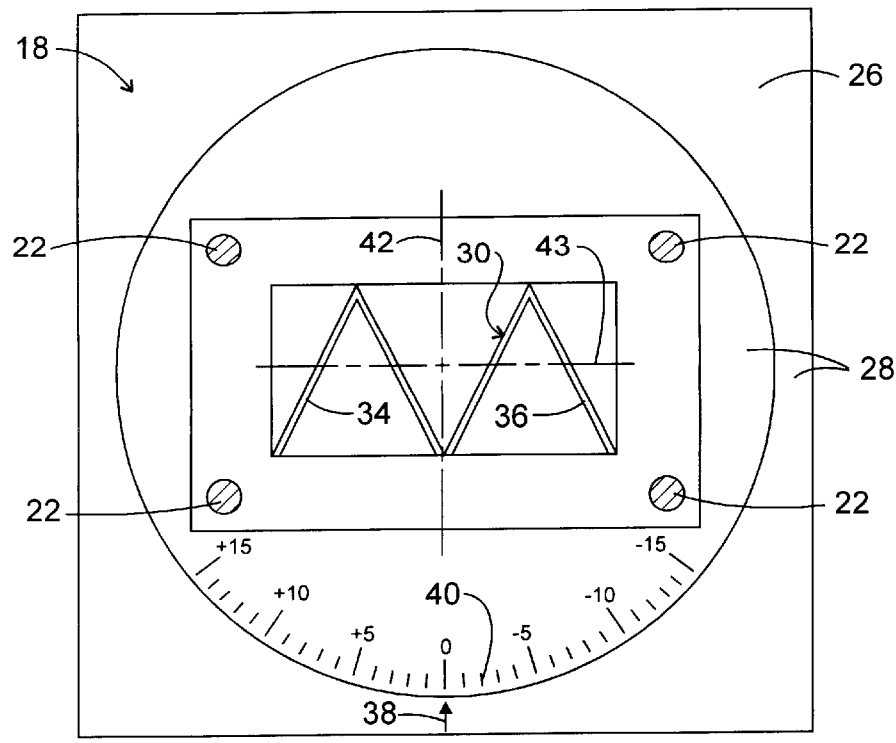
FIG. 6 is a section view taken at line 6—6 of FIG. 5.

Details of double-V reference pattern 30 are best shown in FIGS. 5 and 6. Basically, such reference pattern is comprised of two V-configured elements 34 and 36 with each such "V" being contained within an equally-sized and adjoining imaginary true square. Thus, the angle that is included between the legs of each "V" will be approximately 53 degrees, 8 minutes (2 times are tangent 0.5), and each right-angled distance between the legs of an element 34 or 36 will be equal to its distance from the "V" apex along the "V" axis of symmetry.

For MR imaging applications of the present invention, the legs of "V" elements 34 and 36 are essentially constructed of small-diameter plastic tubes filled with an image-conspicuous sterile contrast agent such as KY jelly. The filled plastic tube legs are secured to the underside of equipment surface antenna 32 (or to base member 28), by conventional permanent adhesive. With respect to CT imaging, all apparatus parts are imaged—metal, plastic, etc.

Also, frame member 26 and base member 28 of subassembly 18 are provided with the respective etched or printed indicia designated 38 and 40, respectively, and such are used in the hereinafter described process of properly aligning base member 28 relative to the plane that contains equipment cross-sectioning image plane 16. Basically, the arrow indicia 38 and the 0 (zero) value of scale indicia 40 each coincide with the illustrated axis of symmetry 42 of double-V reference pattern 30 when the X-axis of needle-device locator subassembly 24 and of body-part compression plate subassembly 20 are at right angles (along line 43) to symmetry axis 42. Reference pattern 30 also has an axis of asymmetry 43 that is oriented at right angles to axis 42.

Body-part compression plate subassembly 20 is basically comprised of a plate member 50 having affixed sleeves 52 (and included sleeve clamping screws) that cooperate with vertical posts 22 and also having interior opening 54 that is filled with a very taut open mesh element 56 which has a very high degree of net open area similar to that of the stringing in a tennis racquet.

Figure 11:
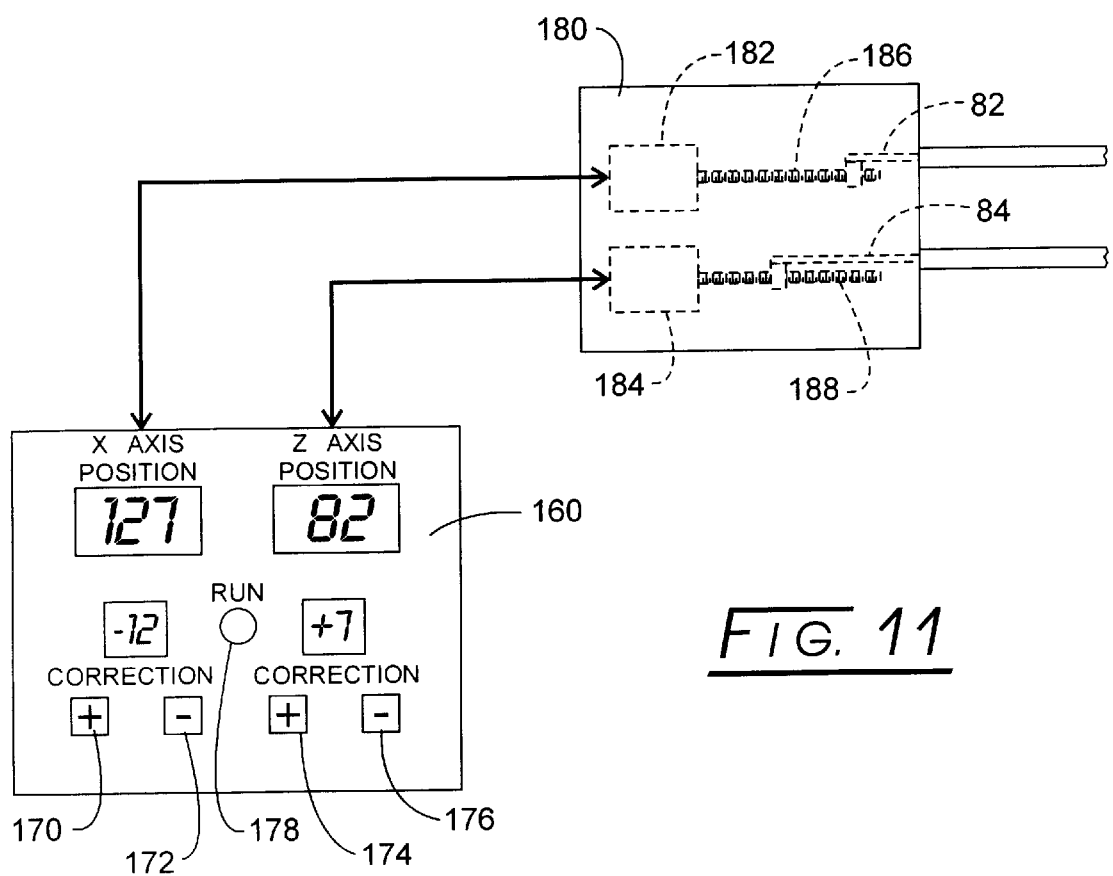
FIG. 11 is a schematic illustration of an automatic servo actuator control that may be utilized to control movement of the ends of the remote control for effecting linear movements of the needle-device guide of FIG. 8 other than manually.

Needle-device locator subassembly 24 is basically comprised of X-axis rails 60 and 62 and Z-axis rail 64, each affixed to plate member 50, and a needle-device guide carrier 66 slidably mounted on rails 60 and 62 and having and internal open slide 68 that co-operates with the Z-axis rails 70 of carrier 66. Located within open slide element 68 is the hereinafter detailed and described readily-removable, needle-device guide subassembly 80 also provided with a double-V reference pattern (see FIG. 8) that differs from double-V reference pattern 30 provided with assist apparatus base member 28. Subassembly 24 also advantageously is provided with a remote control positioner that includes sheathed, push-pull cables 82 and 84. Cable 82 is connected to a Z-axis rail 70 of carrier 66 and functions to move that carrier in X-axis directions; cable 84 is connected to open slide 68 and functions to move that slide in Z-axis directions. Optional clamping screws 86 are provided for securing or locking carrier 66 relative X-axis rails 60 and 62 when it has been moved to its position for subsequent needle-device insertion. In drawing FIGS. 1 and 2, manual manipulation of positioning cables 82 and 84 is contemplated. However, automatic remote actuation and control of positioning cables 82 and 84 is quite feasible and desirable. One manner for accomplishing that objective is schematically illustrated in FIG. 11.

Figure 8:
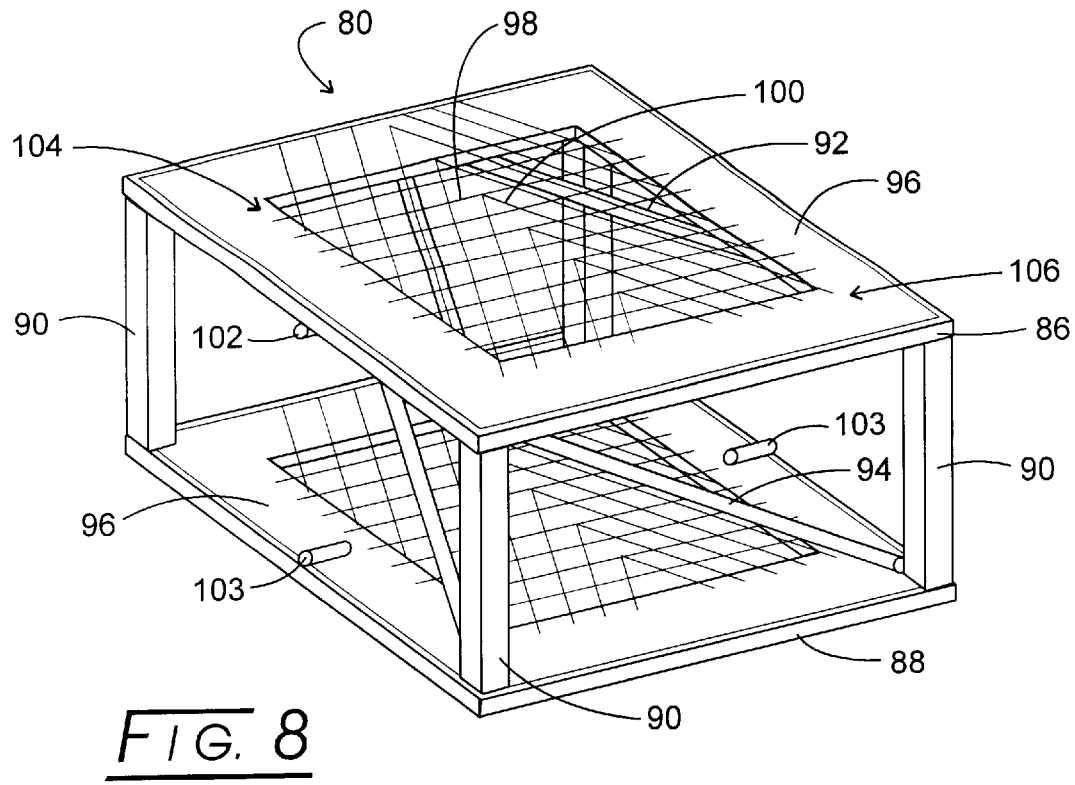
FIG. 8 is a perspective view of the readily-removable and disposable, needle-device guide supported on the needle-device locator subassembly that is secured to the compression plate of the FIG. 3 apparatus.
Figure 9:
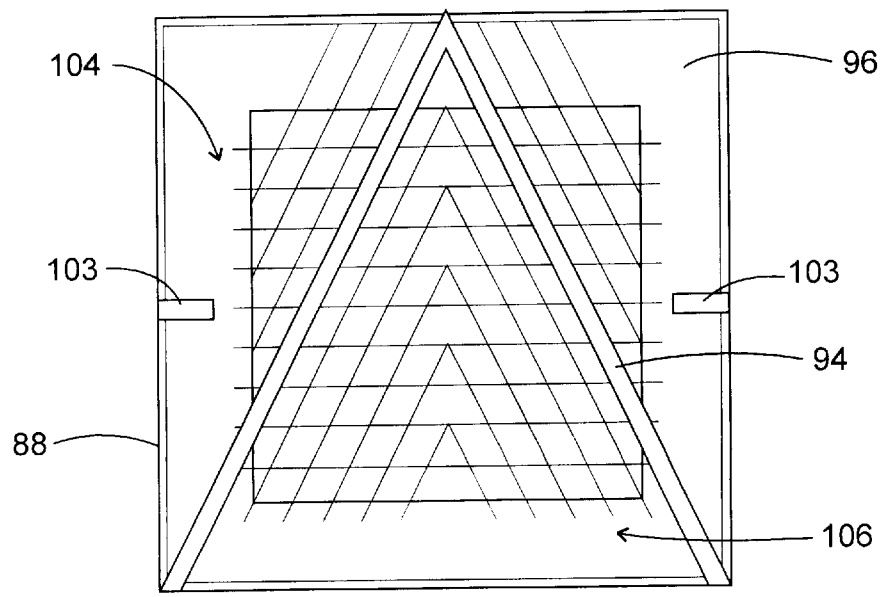
FIG. 9 is a plan view of a face of one of the two face frames of the removable and disposable needle-device guide of FIG. 8.

FIGS. 8 and 9 provide details of readily-removable, needle-device guide subassembly 80. That subassembly includes an open rigid box frame having top and bottom face frames 86 and 88 joined into a unitary structure by side legs 90. The interior faces of face frames 86 and 88 each support an attached V-configured reference pattern element 92 or 94 which together constitute a "stacked" double-V reference pattern. Although V-shaped reference pattern elements 92 and 94 have the same geometric configuration as V-shape elements 34 and 36 of base member 28, such have significantly reduced overall dimensions.

Figure 10:
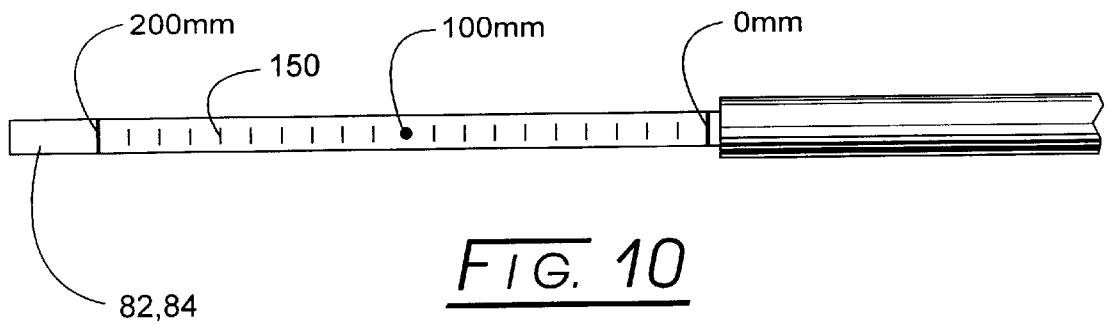
FIG. 10 is a schematic view of a manually-manipulated pushpull cable end of the remote control for effecting linear movements of the needle-device guide of FIG. 8.

Superimposed on and adhered to the exterior face of each of face frames 86 and 88 is a transparent, perforable film or diaphragm element 96 having V-shaped transverse reference lines 98 and angled reference lines 100 printed thereon. Lines 98 conform to the same measurement as the distance between the two image conspicuous limbs 92, 94. Lines 100 are spaced at millimeter distances parallel to the closest image conspicuous limb 92, 94. Short and straight, image-conspicuous, fiduciary elements 102 and 103 are adhered to the inner faces of face frame elements 86 and 88, respectively, and in alignment with one of transverse lines 98 (e.g., the 30 millimeter line), and are available for use in verifying subassembly position accuracy relative to later-described visual scales provided on the remote ends of push-pull positioning cable elements 82 and 84. Refer to FIG. 10. Also, scale 104 is printed on perforable diaphragm elements 96 and are utilized at the time vectoring and inserting the physician-held medical needle-device into needle-device guide subassembly 80 following subassembly location above the patient anatomical target of interest. "V"-elements 92 and 94 are constructed in the same manner as the similar elements of image-conspicuous reference pattern 30, and when being "stacked" are positioned vertically above and below each other. Similarly, it is important that the perforable diaphragms 96 provided in subassembly 80 be positioned in vertical alignment above and below each other.

Figure 7:
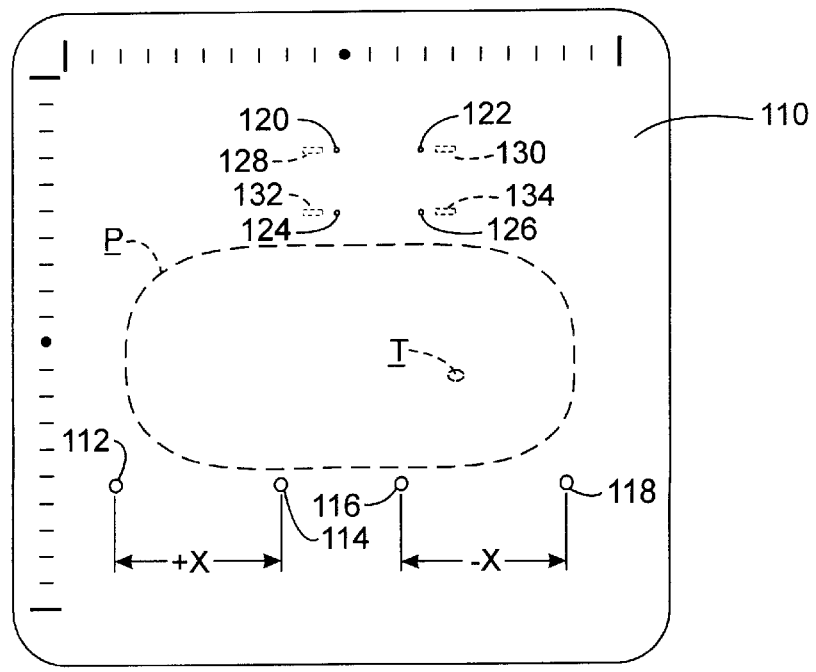
FIG. 7 is a schematic elevation view of the MRI equipment monitor screen showing patient and reference pattern images occurring with the imaging equipment vertical cross-sectional imaging plane positioned at line 5—5 of FIG. 4.

FIG. 7 schematically illustrates the screen 110 of cathode ray tube monitor normally incorporated in MRI equipment 10 with the patient and reference pattern images that are displayed when assist apparatus 12 is properly positioned with respect to equipment cross-sectional imaging plane 16 and plane 16 intersecting the patient P's body at the anatomical target of interest T. Screen 110 specifically displays the leg cross-section images 112 and 114 of V-element 34, the leg cross-section images 116 and 118 of reference pattern element 36, the leg cross-section images 120 and 122 of needle-device guide subassembly upper V-reference pattern 92, and the leg cross-section images 124 and 126 of lower V-reference pattern 94. If the plane of fiduciary reference patterns 102 and 103 of subassembly 80 is vertical and coincides with equipment cross-section image plane 16 containing target T, cross-section images 128 and 130 of the upper face frame element 86 and cross-section images 132 and 134 of lower face frame element 88 will also appear on the screen as shown in FIG. 7.

FIG. 10 schematically illustrates a remote control push-pull cable end detail that may advantageously incorporated into each of control cables 82 and 84. Basically, each cable end is provided with an affixed scale 150 having indicia in units of measurement corresponding to the units of measurement, usually millimeters, and for the full range of movement of carrier element 66 by cable element 82 in the X-axis direction (e.g., 200 millimeters). Only one half of that scale distance (e.g., from 0 to 100 millimeters) is normally used for the movement of open slide element 68 in the Z-axis direction by control cable 84.

FIG. 11 schematically illustrates a remote control for push-pull cables 82 and 84 that does not involve manually moving the cable ends. Instead an automatic control comprised of control box 160 and electrically connected drive box 180 may be advantageously utilized. Control box 160 has display windows 162 and 164 that show the current position co-ordinates of the center of needle-device guide subassembly 80 in their X-axis and Z-axis ranges, respectively, display windows 166 and 168 that show the correction required to locate the center of needle-device guide subassembly over the patient anatomical target of interest by operator manual inputs through +(plus) and –(minus) respective actuating buttons 170, 172, 174, and 176. When the proper correction values are found displayed in windows 166 and 168, start button 178 is manually actuated to start accomplishment of the operator-desired position changes.

Drive box 180 basically includes two bi-directional conventional stepper motors 182 and 184 that are connected to cable ends 82 and 84, respectively, through lead screw drive elements 186 and 188. Electrical power inputs to stepper motors 182 and 184 are controlled by control box 160 and cause cable ends 83 and 84 to be thereby advanced or retracted.

The FIG. 7 display images are used in the procedures of properly locating and orienting apparatus base member 28 and vectoring the to-be-used medical needle-device during its insertion in guide subassembly 80 and subsequent insertion into the imaged body part of patient P.

Figure 14:
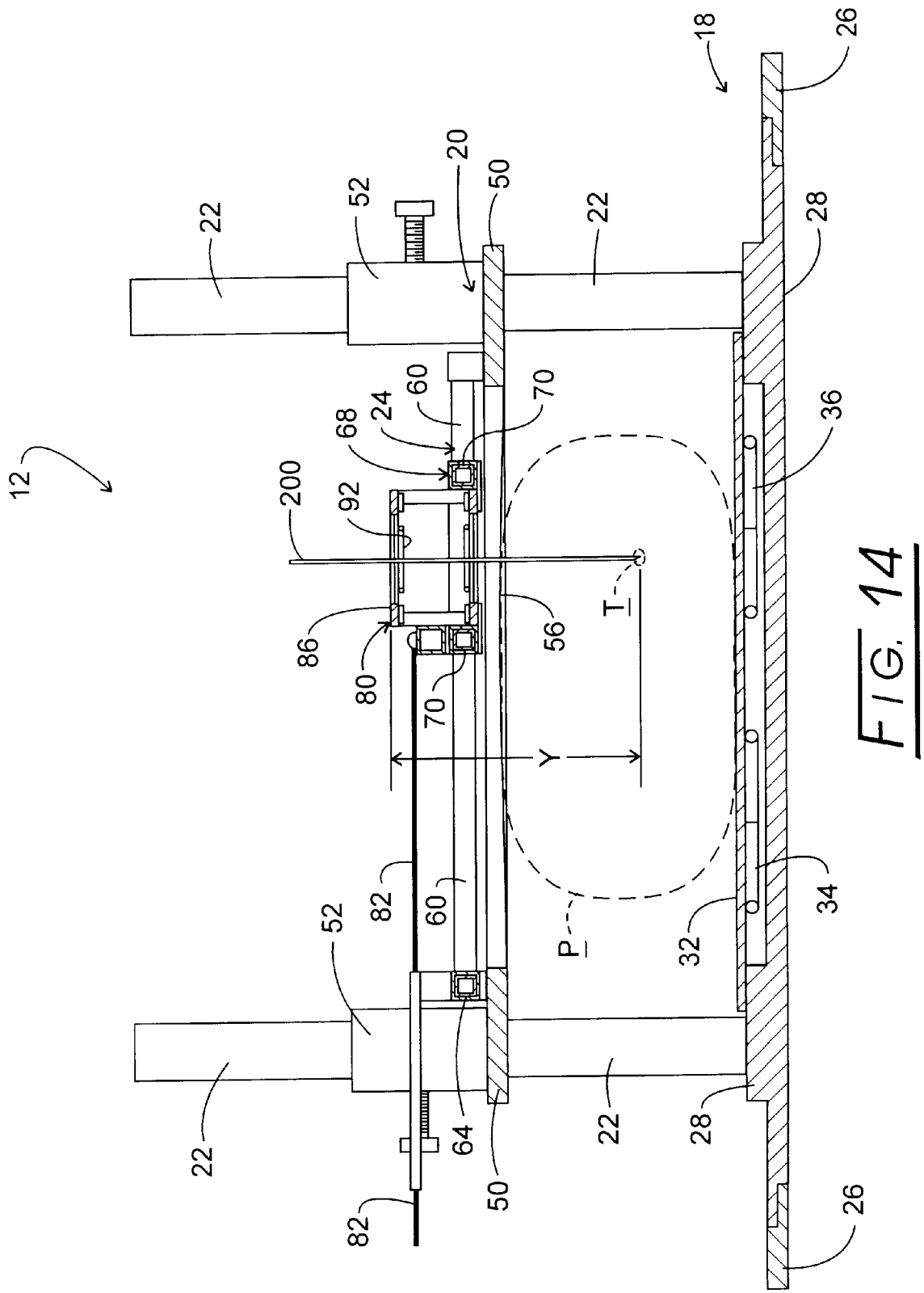
FIG. 14 is a section view similar to that of FIG. 5 but additionally illustrating a medical needle-device inserted in the stereotactic apparatus needle-device guide and contacting the patient anatomical target of interest.

In FIG. 14 I illustrate assist apparatus 12 in elevation and show a medical needle-device 200 positioned with its lower extreme at the patient anatomical target T. The distance Y of that Figure can be measured on the screen 110 of the imaging equipment monitor, and corresponds to the actual distance from the line connecting screen images 120 and 122 to target T. Scaled distance indicia are normally provided on the exterior of needle-device 200 and extend from the device lower tip upward. That scale information may be easily utilized to determine the depth of insertion of needle-device 200 through guide subassembly 80 and into the patient body-part P from the underside of guide upper open face frame 86 to accurately just reach target T.

Figure 12:
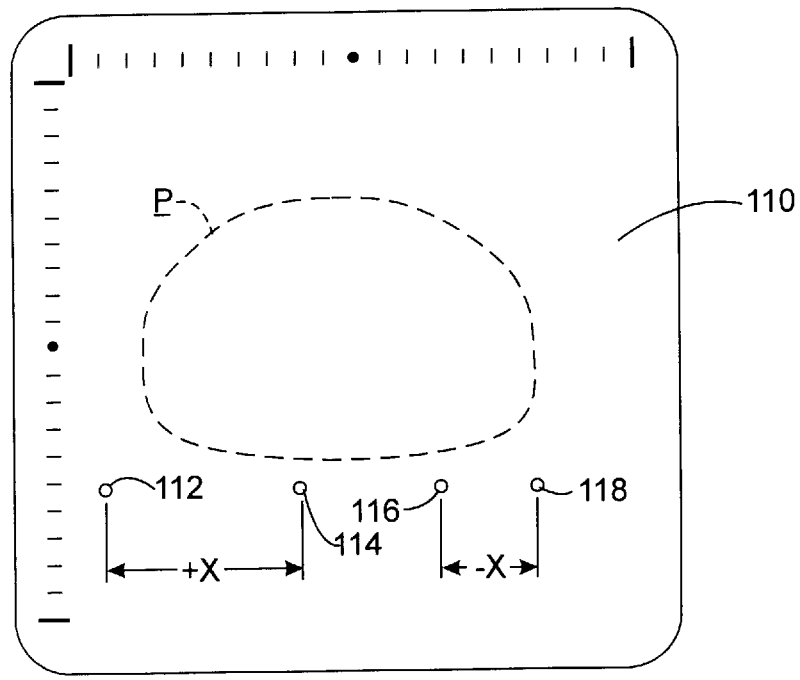
FIG. 12 is an elevation view of the monitor screen of the FIGS. 1 and 2 imaging equipment illustrating base reference pattern images when the apparatus base double-V reference pattern is not properly aligned with the imaging equipment cross-sectional imaging plane.
Figure 13:
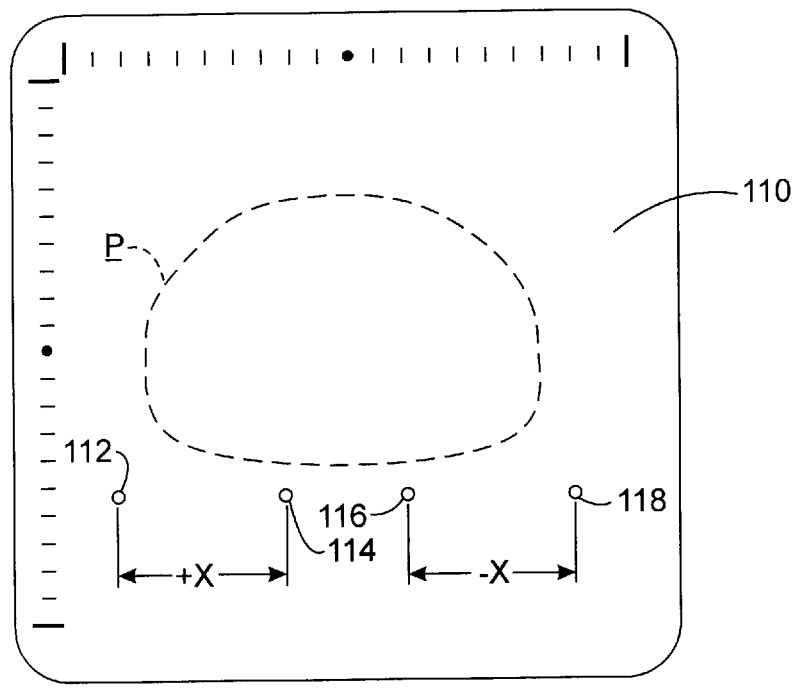
FIG. 13 is an elevation view similar to FIG. 12 but illustrating a properly aligned base reference pattern condition.

The procedure for properly aligning apparatus base member 28 is best understood by reference to FIGS. 12 and 13 which assume that patient P has been positioned on support table 14 as desired and that assist apparatus 12 has been positioned on the table in proximity to the region of the patient anatomical target of interest. Referring to FIG. 12, the distance designated +X between reference pattern images 112 and 114 is first measured and a millimeter magnitude value (e.g., 20 millimeters) found. The distance –X between reference pattern images 116 and 118 is also measured and a millimeter magnitude value (e.g., 10 millimeters) found. The difference between such measured values (e.g., +10 millimeters) is a measurement of the magnitude of rotational correction that is required to place base member 28 in a condition where asymmetry axis 43 of double-V reference pattern 30 lies in a plane that can be made parallel to equipment cross-sectional imaging plane 16.

Using principles of plane geometry pertaining to double-V reference pattern 30 and elemental mathematics, circular scale 40 marked on base member 28 is provided with measurement units that correspond to the millimeter values of the required correcting rotation. Thus, for the assumed FIG. 12 case and with patient support table 14 moved to a position where the physician-user can manually rotate base member 28, the +10 value on scale 40 is brought into alignment with indicia 38 to effect the necessary correction.

When the base member 28 rotational correction is completed, compression plate subassembly 20 is engaged with support posts 22, the patient body-part to be subjected to the medical procedure is compressed by downward movement of subassembly 20 to obtain body-part immobility, subassembly 20 is secured against further sliding along post elements 22, and patient support table 14, patient P, and assist apparatus 12 are returned to the patient body-part imaging position. Reference pattern 30 section images will then appear on display screen 110 with the +X distance between images 112 and 114 being equal to the –X distance between section images 116 and 118 as shown in FIG. 13. The correlation of scale 40 values to the scaled distances between the leg section images of double-V reference pattern 30 is achieved by virtue of the use of reference pattern "V" configurations wherein the angle included between the legs of each "v" is very nearly equal to the previously-indicated 53 degrees, 8 minutes.

The next basic steps to the method of the present invention involve properly positioning needle-device locator subassembly 24 and determining the vector and depth at which the to-be-used medical needle device is to be inserted into needle-device guide subassembly 80 for subsequent insertion into the patient body-part to accurately reach the patient anatomical target of interest.

Generally, the next step involves taking successive images that in effect move cross-section imaging plane 16 in a Z-axis direction until that plane, as viewed on the imaging equipment monitor screen, intersects and contains the patient body-part target of interest T. Subsequently and using push-pull cables 82 and 84 from a remote position, the physician user moves both guide carrier element 66 and open slide element 68 to a position where the cross-section images 120, 122, 124, and 126 of V-shape reference patterns 92 and 94 appear on the imaging equipment monitor screen 110 (see FIG. 7), and where a vertical or near-vertical line passing midway between images 120 and 122 and midway between images 124 and 126 intersects the patient target T. If the measured distance between reference pattern images 120 and 122 (e.g., 30 millimeters) equals the distance measured between section images 124 and 126 (also 30 millimeters), the to-be-inserted medical-device needle is to be projected through the transparent perforable diaphragms 96 of removable guide subassembly 80 at the centers of the marked transverse lines that numerically correspond to the measured distances (e.g., 30 millimeters) and are so-indicated in the printed marginal scales of face frames 86 and 88.

If the measured distance between section images 120 and 122 (e.g., 30 millimeters) is greater or less than the distance measured between section images 124 and 126 (e.g., 25 millimeters or 35 millimeters), the to-be-inserted medical-device needle is to be projected through the transparent perforable diaphragms 96 of removable guide subassembly 80 at the center of the marked transverse line that numerically corresponds to the measured distance (e.g., 30 millimeters) so-indicated in the printed marginal scale of face frame 86, and at the center of the marked transverse line that numerically corresponds to the measured distance (e.g., 25 millimeters or 35 millimeters) so-indicated in the printed marginal face frame 88 of needle-device guide subassembly 80.

As a matter of convenience and in cases where the needle-device insertion is not to be centered between the pairs of cross-section images (where the successive printed "V" apexes are positioned on diaphragm elements 96) but instead nearer to one of the two legs or limbs of the V-shape reference pattern, the desired distance of off-set may be measured on monitor screen 110 and implemented by counting the modular lengths that extend along the diaphragm transverse reference lines—each modular length corresponding to the unit distance between adjacent transverse lines (e.g., 5 millimeters).

I claim my invention as follows:

1. In a stereotactic apparatus for use in a medical procedure that also involves the use of medical imaging equipment having a cross-sectional imaging plane and a monitor which displays a patient cross-sectional image taken at the equipment cross-sectional imaging plane, in combination:

an apparatus base member adapted to be placed in a fixed position relative to the equipment cross-sectional imaging plane and in the vicinity of a patient internal anatomical target of interest; and an image-conspicuous reference pattern supported by said apparatus base member and having a double-V platform configuration, said double-V reference pattern, when sectioned by the medical imaging equipment cross-sectional image plane, being shown on the medical imaging equipment monitor by section images that quantify the angularity of said reference pattern relative to the medical imaging equipment cross-sectional imaging plane.

2. The stereotactic apparatus defined by claim 1 wherein said double-V reference pattern includes pattern elements which intersect each other at an angle of approximately fifty-three degrees.

3. A stereotactic apparatus assembly for use in a medical procedure that also involves the use of medical imaging equipment having a cross-sectional imaging plane and a monitor which displays a patient cross-sectional image taken at the equipment cross-sectional imaging plane, and comprising:

an apparatus base member adapted to be fixedly placed relative to the cross-sectional imaging plane of the medical imaging equipment and in the vicinity of a patient internal anatomical target of interest; and an image-conspicuous reference pattern supported by said apparatus base member and having a double-V platform configuration, a compression plate member adjustably movable relative to said apparatus base member and having an interior open area through which a medical needle-device may be passed;

a needle-device locator subassembly supported by said compression plate member, surrounding said compression plate member internal open area, and having a needle-device guide carrier mounted for linear movement in orthogonal co-ordinate directions;

a needle-device guide member removably mounted on said locator subassembly needle-device guide carrier and having an image-conspicuous double-V reference pattern;

said base double-V reference pattern, when sectioned by the medical imaging equipment cross-sectional image plane, being shown on the medical imaging equipment monitor by section images that quantify the angularity of said base double-V reference pattern relative to the medical imaging equipment cross-sectional imaging plane, and said needle-device guide member double-V reference pattern, when sectioned by the medical imaging equipment cross-sectional image plane, being shown on the medical imaging equipment monitor by section images that, together with the image of the patient internal anatomical target of interest, quantify the distance of separation and angularity of said needle-device guide member relative to the patient internal anatomical target of interest.

4. The stereotactic apparatus assembly defined by claim 3 wherein said needle-device guide member has an open upper face frame, an open lower face frame spaced apart from and parallel to said open upper face frame, a pair of image-conspicuous, V-shaped reference patterns carried respectively by said open upper face frame and said open lower face frame, and a pair of perforable diaphragm elements covering respectively said open upper face frame and said open lower face frame, the individual reference patterns of said pair of image-conspicuous, V-shaped reference patterns being vertically aligned with each other and each having an internal angle of approximately 53 degrees, and said pair of perforable diaphragm elements each having printed transverse lines and an accompanying scale indicating the perpendicular distance of each transverse line from the apex of its adjacent individual V-shaped reference pattern.

5. The stereotactic apparatus defined by claim 3 wherein said base double-V reference pattern and said needle-device guide member double-V reference pattern each include pattern elements which intersect each other at an angle of approximately fifty-three degrees.

6. The stereotactic apparatus defined by claim 3 and further comprised of position control means connected to said locator subassembly needle-device guide carrier, said position control means having push-pull cable means manipulated at a position remote from said apparatus base member.

7. The stereotactic apparatus defined by claim 6, and further comprising calibrated scale means affixed to said push-pull cable means, said calibrated scale means being incrementally calibrated in measurement units over a range that corresponds to the range and calibrated measurement units of said locator subassembly along coordinate orthogonal directions.

8. The stereotactic apparatus defined by claim 3 and further comprised of position control means connected to said locator subassembly needle-device guide carrier, said position control means having closed-loop servo control actuators positioned remote from said apparatus base member and operably connected to said locator subassembly by push-pull cable means.

9. The stereotactic apparatus of claim 3 wherein said compression plate member interior open area is partially defined by a thin generally rigid grid member.

10. The stereotactic apparatus of claim 3 wherein said medical needle device is mounted at a fixed known position on said needle-device guide member such that said medical needle device will always be at a known position in relation to said cross-sectional image plane.

11. A stereotactic apparatus assembly needle-device guide member comprising:

an open upper face frame;

an open lower face frame spaced apart from and parallel to said open upper face frame;

a pair of image-conspicuous, V-shaped reference patterns carried respectively by said open upper face frame and said open lower face frame; and a pair of perforable diaphragm elements covering respectively said open upper face frame and said open lower face frame, said pair of image-conspicuous, V-shaped reference patterns being vertically aligned with respect to each other and each having an internal angle of approximately 53 degrees, and said pair of perforable diaphragm elements each having printed transverse lines and an accompanying scale indicating the perpendicular distance of each transverse line from the apex of its adjacent individual V-shaped reference pattern.

* * * * *